(12) United States Patent
Tassoni et al.

(10) Patent No.: US 10,238,396 B2
(45) Date of Patent: Mar. 26, 2019

(54) DELIVERY DEVICE FOR USE WITH AN EMBOLIC COIL DEVICE AND METHODS FOR MAKING AND USING THE SAME

(71) Applicant: BOSTON SCIENTIFIC SCIMED, INC., Maple Grove, MN (US)

(72) Inventors: Nicholas L. Tassoni, Andover, MN (US); Mary-Claire Anderson, Excelsior, MN (US); Gary J. Pederson, Jr., Albertville, MN (US); Ken Xiao Kang Zhang, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 125 days.

(21) Appl. No.: 15/297,423

(22) Filed: Oct. 19, 2016

(65) Prior Publication Data

US 2017/0112500 A1    Apr. 27, 2017

Related U.S. Application Data

(60) Provisional application No. 62/244,570, filed on Oct. 21, 2015.

(51) Int. Cl.
*A61B 17/12* (2006.01)
*A61B 90/00* (2016.01)

(52) U.S. Cl.
CPC ...... *A61B 17/1214* (2013.01); *A61B 17/1215* (2013.01); *A61B 17/12031* (2013.01); *A61B 17/12113* (2013.01); *A61B 90/39* (2016.02); *A61B 2017/1205* (2013.01); *A61B 2017/12054* (2013.01); *A61B 2090/3966* (2016.02)

(58) Field of Classification Search
CPC .............. A61B 17/1214; A61B 90/39; A61B 17/121113; A61B 17/1215
See application file for complete search history.

(56) References Cited

U.S. PATENT DOCUMENTS

| | | |
|---|---|---|
| 5,261,916 A | 11/1993 | Engelson |
| 5,417,708 A | 5/1995 | Hall et al. |
| 5,639,277 A | 6/1997 | Mariant et al. |
| 5,891,130 A | 4/1999 | Palermo et al. |
| 5,895,391 A | 4/1999 | Farnholtz |
| 5,925,059 A | 7/1999 | Palmero et al. |

(Continued)

FOREIGN PATENT DOCUMENTS

| | | |
|---|---|---|
| WO | 2008085606 A1 | 7/2008 |
| WO | 2010009019 A1 | 1/2010 |

*Primary Examiner* — Tuan V Nguyen
(74) *Attorney, Agent, or Firm* — Seager, Tufte & Wickhem, LLP

(57) ABSTRACT

An embolic coil delivery assembly is disclosed. The delivery system may include a tubular member having a distal portion, a proximal portion and a lumen extending therein. The system may further include a tip member secured to the tubular member. The tip member may include a distal portion and a bonding portion. The bonding portion may include a bonding surface. The system may also include an embolic coil releasably disposed within the distal portion of the tip member. The distal portion of the tubular member may extend over the bonding portion of the tip member. The bonding surface may be configured to mechanically interlock with the tubular member.

8 Claims, 10 Drawing Sheets

(56) References Cited

U.S. PATENT DOCUMENTS

| | | |
|---|---|---|
| 7,485,122 B2 | 2/2009 | Teoh |
| 8,202,292 B2 | 6/2012 | Kellett |
| 8,328,860 B2 | 12/2012 | Strauss et al. |
| 8,333,796 B2 | 12/2012 | Tompkins et al. |
| 2006/0276832 A1 | 12/2006 | Balgobin et al. |
| 2007/0288049 A1* | 12/2007 | Davis ............... A61B 17/12022 606/191 |

* cited by examiner

DELIVERY DEVICE FOR USE WITH AN EMBOLIC COIL DEVICE AND METHODS FOR MAKING AND USING THE SAME

CROSS-REFERENCE TO RELATED APPLICATIONS

This application claims priority under 35 U.S.C. § 119 to U.S. Provisional Application Ser. No. 62/244,570, filed Oct. 21, 2015, the entirety of which is incorporated herein by reference.

FIELD OF THE INVENTION

The present disclosure pertains to delivery devices for use with an embolic coil device. More particularly, the present disclosure pertains to design, material, manufacturing method, packaging, and use alternatives for embolic coil and delivery devices.

BACKGROUND

A wide variety of delivery devices have been developed for medical use including, for example, aiding in the delivery of an embolic coil device. These delivery devices are manufactured, packaged, and used according to any one of a variety of different methods. Of the known delivery devices and methods, each has certain advantages and disadvantages. There is an ongoing need to provide alternative delivery devices as well as alternative methods for manufacturing, packaging, and using delivery devices.

BRIEF SUMMARY

The disclosure provides design, material, manufacturing method, packaging, and use alternatives for an embolic coil, embolic coil delivery devices, and the like. An example embolic coil delivery assembly comprises:

a tubular member having a distal portion, a proximal portion and a lumen extending therein;

a tip member secured to the tubular member, the tip member including a distal portion and a bonding portion, the bonding portion including a bonding surface; and an embolic coil releasably disposed within the distal portion of the tip member;

wherein the distal portion of the tubular member extends over the bonding portion of the tip member;

wherein the bonding surface is configured to mechanically interlock with the tubular member.

Alternatively or additionally to any of the embodiments above, wherein the bonding portion includes a coil.

Alternatively or additionally to any of the embodiments above, wherein the bonding portion includes a coil having a plurality of windings, the plurality of windings being configured to mechanically interlock with the tubular member.

Alternatively or additionally to any of the embodiments above, wherein the tubular member further comprises an inner surface, wherein the inner surface interlocks with the plurality of windings.

Alternatively or additionally to any of the embodiments above, wherein the inner surface of the tubular member includes an inwardly extending member, and wherein the inwardly extending member extends between two of the plurality of windings.

Alternatively or additionally to any of the embodiments above, wherein the distal portion of the tip member includes a first flexibility and the bonding portion includes a second flexibility different from the first flexibility.

Alternatively or additionally to any of the embodiments above, wherein the bonding portion includes one or more of slits, teeth, grooves, lattice, slots, texture and dimples.

Alternatively or additionally to any of the embodiments above, wherein the bonding portion of the tip member includes an outwardly extending member, and wherein the outwardly extending member is configured to mechanically interlock with an inner surface of the tubular member.

Alternatively or additionally to any of the embodiments above, wherein the distal portion of the tip member includes a first wall thickness and the bonding portion of the tip member includes a second wall thickness different from the first wall thickness, wherein the second wall thickness is configured to provide a flexibility that is greater than the first wall thickness.

Alternatively or additionally to any of the embodiments above, wherein the distal portion of the tip member further includes an aperture directed radially away from a longitudinal axis of the tip member.

Alternatively or additionally to any of the embodiments above, wherein the distal portion of the tip member includes an outer surface, and inner surface and a tubular wall extending therebetween, and wherein the aperture extends through at least a portion of the tubular wall.

Alternatively or additionally to any of the embodiments above, wherein the tip member includes a lumen extending therein, and wherein the lumen of the tip member is substantially aligned with the lumen of the tubular member.

Alternatively or additionally to any of the embodiments above, wherein the tubular member includes an outer diameter and wherein the distal portion of the tip member includes an outer diameter substantially equal to the outer diameter of the tubular member.

Alternatively or additionally to any of the embodiments above, further comprising a pull wire disposed within at least a portion of the lumen of the tubular member.

Alternatively or additionally to any of the embodiments above, wherein proximal retraction of the pull wire releases the embolic coil.

Another example embolic coil delivery assembly comprises:

a tubular member including a longitudinal axis and a distal portion having a lumen extending therein, wherein the tubular member includes an inner surface and one or more engagement regions extending radially inward from the inner surface;

a transition member secured to the tubular member, the transition member including a distal portion and a bonding portion, the bonding portion including a first portion disposed along the inner surface and a second portion radially spaced from the inner surface; and an embolic coil disposed within the transition member;

wherein the one or more engagement regions engage both the first and second portions of the bonding surface.

Alternatively or additionally to any of the embodiments above, wherein the distal portion of the transition member includes a first flexibility and the bonding portion of the transition member includes a second flexibility different from the first flexibility.

Alternatively or additionally to any of the embodiments above, wherein the distal portion of the transition member further includes an aperture directed radially away from a longitudinal axis of the tip member.

Alternatively or additionally to any of the embodiments above, wherein the bonding portion of the transition member includes one or more of slits, teeth, grooves, lattice, slots, texture and dimples.

An example catheter for delivering an embolic coil comprises:

a tubular member having a distal portion, a proximal portion and a lumen extending therein;

a delivery tip member including a distal portion and a proximal portion, wherein the proximal portion is disposed within the lumen of the tubular member; and an embolic coil coupled to the delivery tip;

wherein the distal portion of the delivery tip has a first flexibility and the proximal portion of the delivery tip has a second flexibility different from the first flexibility.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description of various embodiments of the disclosure in connection with the accompanying drawings, in which.

Figure 1:
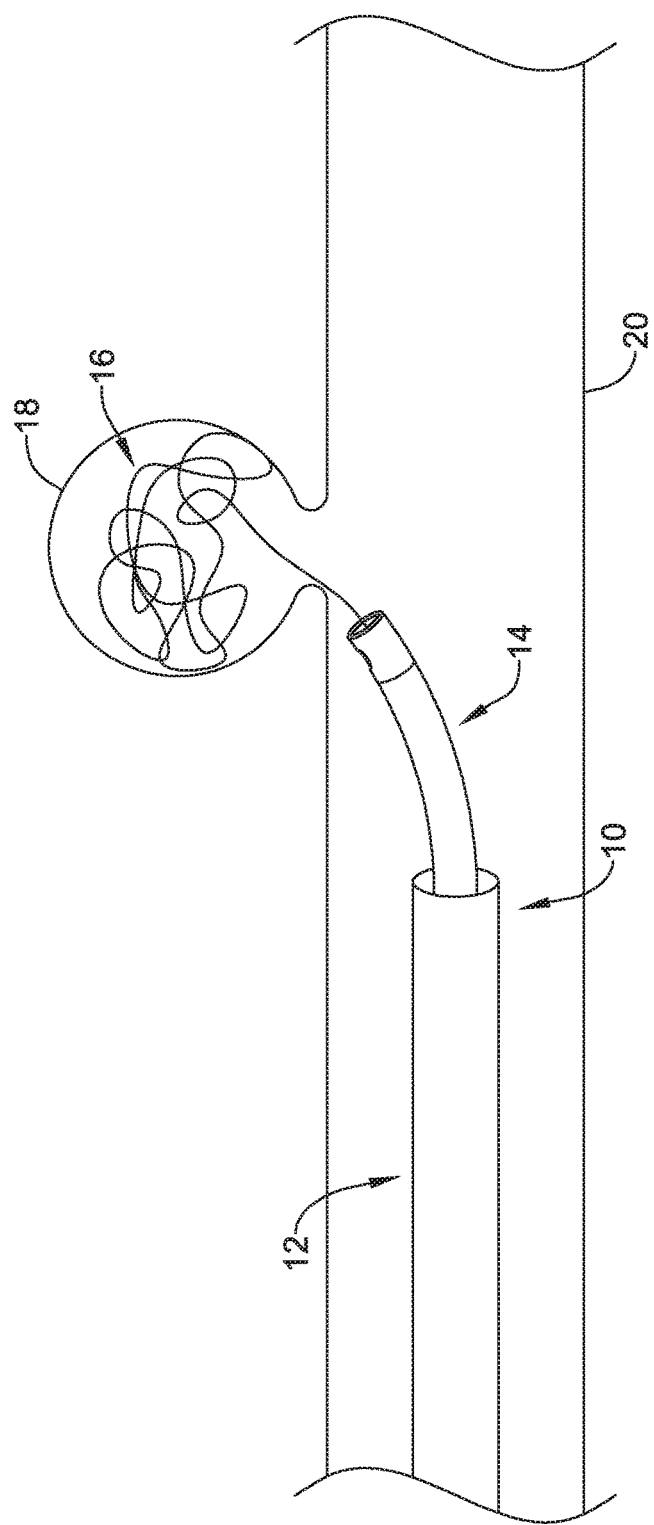
FIG. 1 illustrates an example embolic coil delivery device disposed in a blood vessel.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the disclosure. Any feature of any example embodiment may be incorporated into any other embodiment, as appropriate, unless clearly stated to the contrary.

FIG. 1 shows an example medical device 10, for example an embolic coil delivery system, disposed in a blood vessel 20. Delivery system 10 may include a catheter (e.g. microcatheter) 12 that may be generally configured for advancing within the anatomy of a patient to a position adjacent an area of interest, for example, an aneurysm 18. Catheter 12 may resemble catheters used in the art and they may be sized for the appropriate intervention. As such, it should be understood that there may be a broad range of possible catheter and catheter shaft constructions that may be used. For example, if catheter 12 is intended to treat aneurysm 18 in a particular portion of the vasculature, catheter 12 may be appropriately sized to effectively access that portion of the vasculature.

Figure 2:
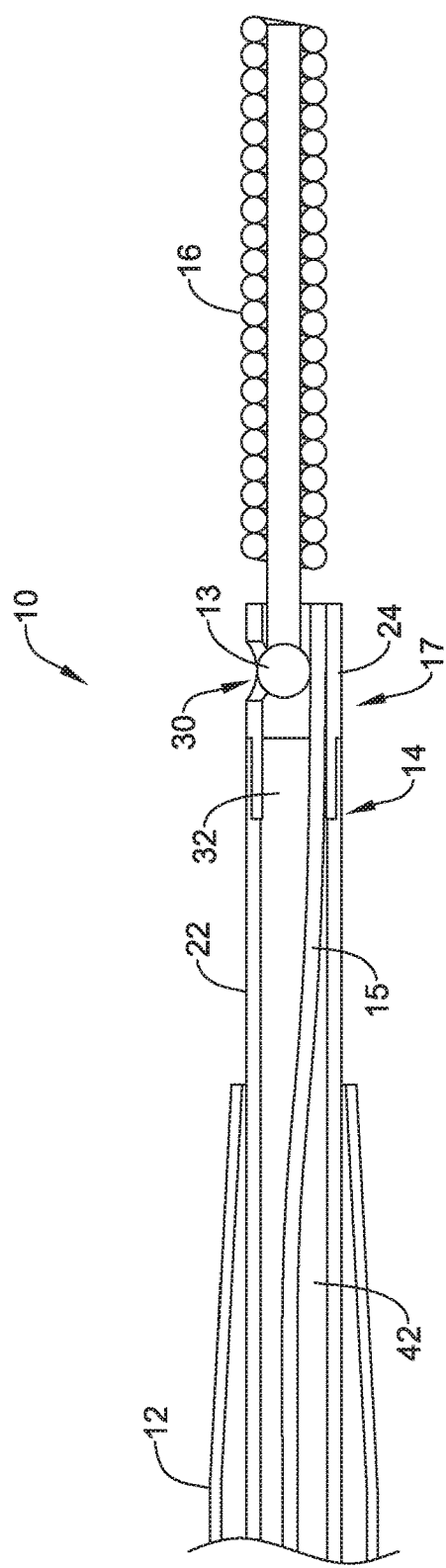
FIG. 2 is a cross-sectional view of an example embolic coil delivery device.

System 10 may include an embolic coil device or other device that may be used to diagnose and/or treat aneurysm 18. The embolic coil device may include an occlusion device or embolic coil 16 that may be coupled to a delivery catheter 14 by, for example, a detachment mechanism 17 as shown in FIG. 2. Detachment mechanism 17 may include a delivery wire 15 and detachable sphere 13 positioned in lumen 32 of the distal portion of delivery catheter 14. Delivery wire 15 may have a substantially constant outer diameter or it may include one or more tapers. Delivery wire 15 may be formed of any suitable material including any of those listed herein. In some embodiments, delivery wire 15 may be coated with a lubricious coating (not shown), which may reduce friction during delivery of occlusion device 16. Detachable sphere 13 may be coupled to embolic coil 16. For example, sphere 13 may be connected to a proximal portion of embolic coil 16. In some instances, sphere 13 may be releasably coupled to embolic coil 16. In other words, in some instances sphere 13 may separate from embolic coil 16 upon the deployment of embolic coil 16.

Detachment mechanism 17 may be designed such that sphere 13 may be held in place (e.g., held within the distal portion of delivery catheter 14) through a friction or interface fit with delivery wire 15. For example, delivery wire 15 may be positioned adjacent to sphere 13 (e.g., positioned between sphere 13 and an inner surface catheter 14) such that delivery wire 15 effectively locks sphere 13 between the delivery wire 15 and the inner surface of lumen 32 of delivery catheter 14. Additionally, sphere 13 may be positioned adjacent to sidehole 30 (e.g., extending partially within sidehole 30) located in a distal portion of delivery catheter 14. In some examples, sidehole 30 may be defined as an aperture extending through a portion or all of the tubular wall of delivery catheter 14. Aperture 30 may extend radially away from a longitudinal axis of the delivery catheter 14.

The process of delivering embolic coil 16 to the appropriate portion of the anatomy may include detaching embolic coil 16 from delivery catheter 14 (e.g., via detachment of mechanism 17). In some instances, proximal retraction of delivery wire 15 may release sphere 13, thereby allowing embolic coil 16 to separate from delivery catheter 14 at a desired time.

In some instances, delivery catheter 14 along with embolic coil 16 may be positioned within a distal portion of delivery catheter 14 while catheter 12 is advanced to a position adjacent an area of interest. After being positioned adjacent an area of interest, delivery catheter 14 and embolic coil 16 may be advanced out of and away from the distal portion of catheter 12 to an area of interest (e.g., aneurysm 18). However, embolic coil 16 may remain coupled to delivery catheter 14 until delivery wire 15 is proximally retracted such that sphere 13 is completely detached. In other words, until sphere 13 is released via manipulation of delivery wire 15, embolic coil 16 may be retracted and/or recaptured back into the distal portion of catheter 12. Some examples of suitable detachable interface constructions can be found in U.S. Pat. No. 5,895,391, the entire disclosures of which is herein incorporated by reference.

In at least some embodiments, embolic coil 16 may include a variety of different designs and/or configurations. For example, embolic coil 16 may be about 1 to about 60 cm in length it may have a sufficient flexibility such that embolic coil 16 may be capable of deforming and folding and/or bending within a vascular cavity such as aneurysm 18. Embolic coil 16 may be pliable and its overall shape may be easily deformed. For example, when inserted into catheter 12, embolic coil 16 may be easily straightened to lie axially within the lumen of catheter 12. Once disposed outside of or advanced out from the distal tip of catheter 12, embolic coil 16 may convert into a shapelier, nonlinear form such as shown in FIG. 1, and may be loosely deformed to the interior shape of a vascular cavity. Embolic coil 16 may be formed of any suitable material including any of those listed herein. Additionally, embolic coil 16, or a portion thereof, may be coated with a thrombogenic agent, a drug or medication, a biological agent, and the like, or any other suitable coating.

Figure 3:
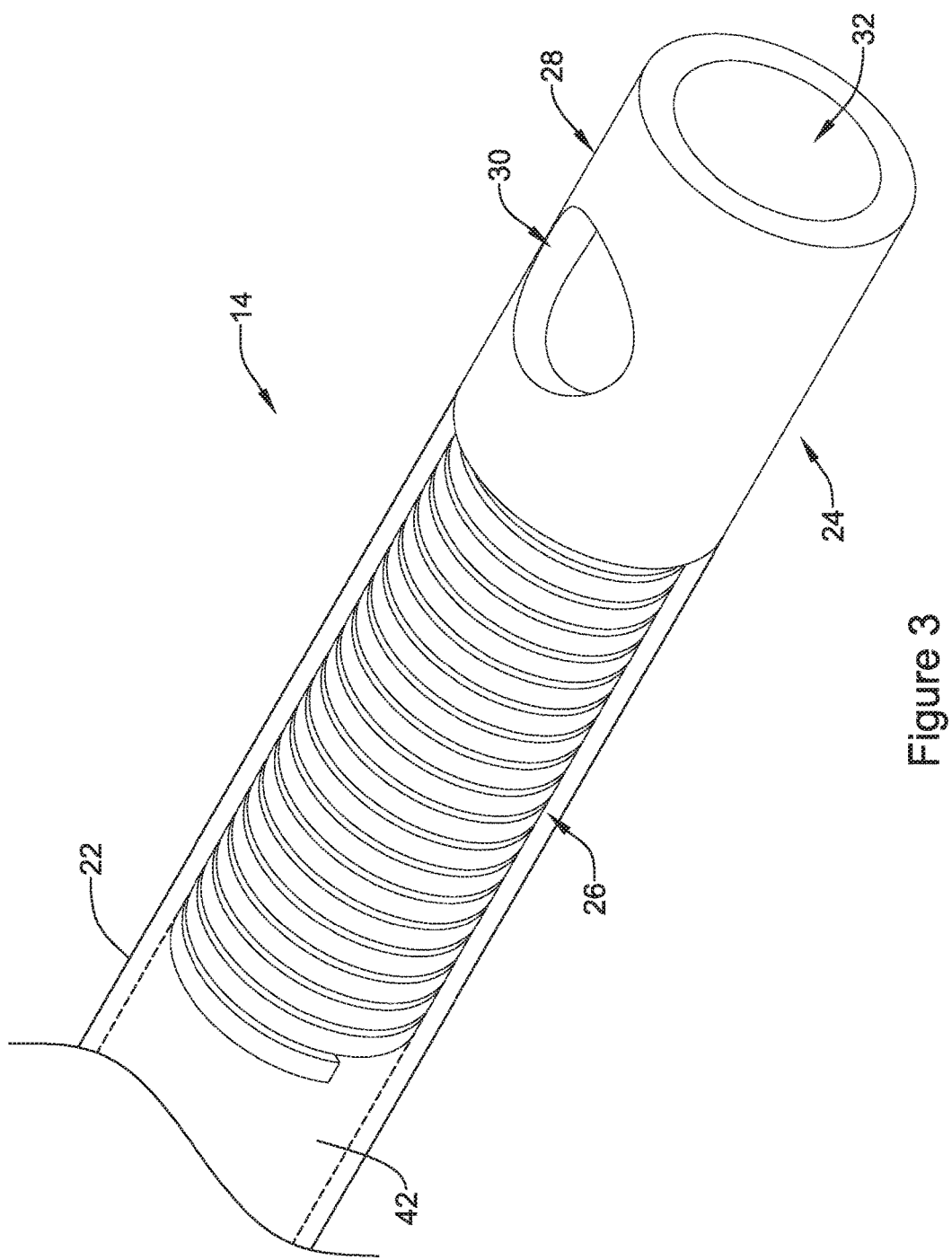
FIG. 3 is a perspective view of an example delivery catheter including a tip member coupled to a tubular member.

FIG. 3 illustrates an enlarged view of the distal end portion of delivery catheter 14. The distal end portion of delivery catheter 14 may include a tip member 24. A portion of tip member 24 may be disposed and/or secured within tubular member 22. Together, tip member 24 and tubular member 22 may define the distal end portion of delivery catheter 14.

Figure 4:
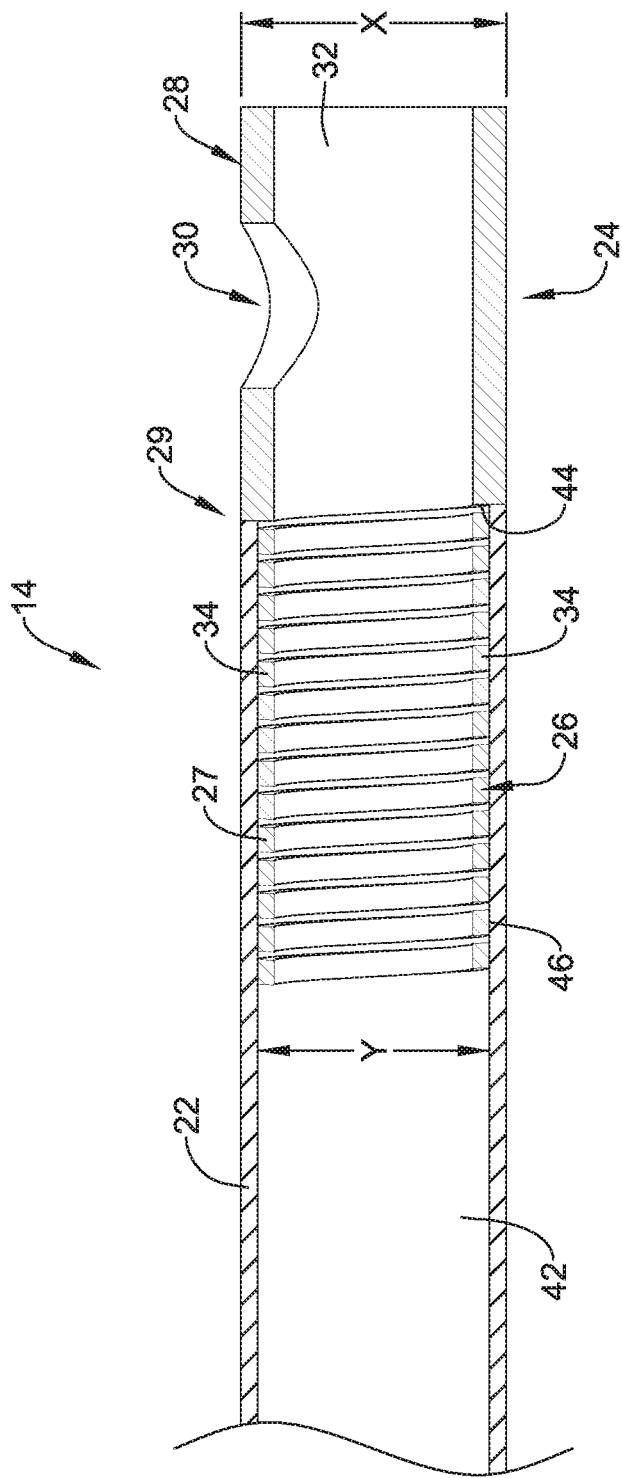
FIG. 4 is a cross-sectional view of an example tip member and a tubular member.

FIG. 4 shows tip member 24 coupled to tubular member 22. Tip member 24 may include a distal tip portion 28 and a bonding portion 26 positioned proximal of distal tip portion 28. In some examples, bonding portion 26 may be referred to as a "ledge" or "ledge portion." Distal tip portion 28 may include an outer diameter illustrated as "X" in FIG. 4. Similarly, bonding portion 26 may include an outer diameter illustrated as "Y" in FIG. 4. In some examples (such as that shown in FIG. 4), outer diameter X of distal portion 28 may be greater than the outer diameter Y of bonding portion 26. The difference between the outer diameter dimensions of distal portion 28 and bonding portion 26 may define a shoulder portion 44. Shoulder portion 44 may include a surface that extends substantially perpendicular to both the bonding portion 26 and/or distal portion 28 surfaces.

In some examples, distal tip portion 28 may include a wall thickness different from the wall thickness defined by bonding portion 26. In particular, the wall thickness of the distal tip portion 28 may be greater than the wall thickness of bonding portion 26. The difference in wall thickness may correspond to a difference in flexibility of the distal tip portion 28 as compared to the bonding portion 26. For example, the flexibility of the bonding portion 26 may be greater than the flexibility of the distal tip portion 28.

As stated above, tip member 24 may include a lumen 32 extending therein (shown as lumen 32). Lumens 32 may substantially align with lumen 42 of tubular member 22. Further, lumens 42 and 32 of the tubular member 22 and tip member 24 may be designed to have one or more of embolic coil 16, detachment mechanism 17, delivery wire 15 and or sphere 13 positioned therein.

As shown in FIG. 4, bonding portion 26 may extend into lumen 42 of tubular member 22. In some instances, the arrangement, overlap, and/or interface of the bonding portion 26 and the tubular member may directly contribute to the flexibility of the distal portion of delivery catheter 14. Therefore, in some instances it may be desirable to increase the flexibility of one or more portions of the catheter 14 (e.g., distal tip member 24) in order to increase the flexibility of the distal portion of catheter 14 without compromising other desirable design attributes of system 10.

To that end, FIG. 4 shows bonding portion 26 including a coil 27 having coil filaments (e.g., windings) 34. Coil windings 34 may be coupled to the proximal portion of the distal portion 28. While coil 27 shown in FIG. 4 may include a single filament 34, it is contemplated that the coil 27 may include one or more coil filaments 34. Further, multiple coil filaments 34 may be interwound with one another along the length of bonding portion 26.

In some instances, coil 27 may provide increased flexibility as compared to a solid member of similar dimensions. Further, in some instances coil 27 may provide the same or increased flexibility over a solid member having a much shorter length. Therefore, in some examples coil 27 may include a larger surface area for coupling tip member 24 to tubular member 22 without sacrificing flexibility. In other words, coil member 27 may provide a more robust connection between tip member 24 and tubular member 22 without decreasing the flexibility of the distal portion of catheter 14 (as compared to a similarly dimensioned solid member).

FIG. 4 shows the distal portion of tubular member 22 extending over bonding portion 26 of tip member 24. As can be seen in FIG. 4, the outer surface of bonding portion 26 (e.g., the outer surface of coil 27) extends along and/or forms an interface region 46 with the inner surface of tubular member 22. In some instances the outer surface of bonding region 26 may contact the inner surface of the distal portion of tubular member 22 along interface region 46.

As illustrated in FIG. 4, the distal end 29 of tubular member 22 may abut and/or mate with shoulder portion 44. For example, the wall thickness of tubular member 22 may be configured such that the outer surface of tubular member 22 may be substantially flush with the outer surface of the distal portion 28 of tip member 24 when then distal end 29 of tubular member 22 abuts shoulder 44. In other words, in some instances the wall thickness of tubular member 22 may be substantially equal to the "height" of shoulder 44.

Figure 5:
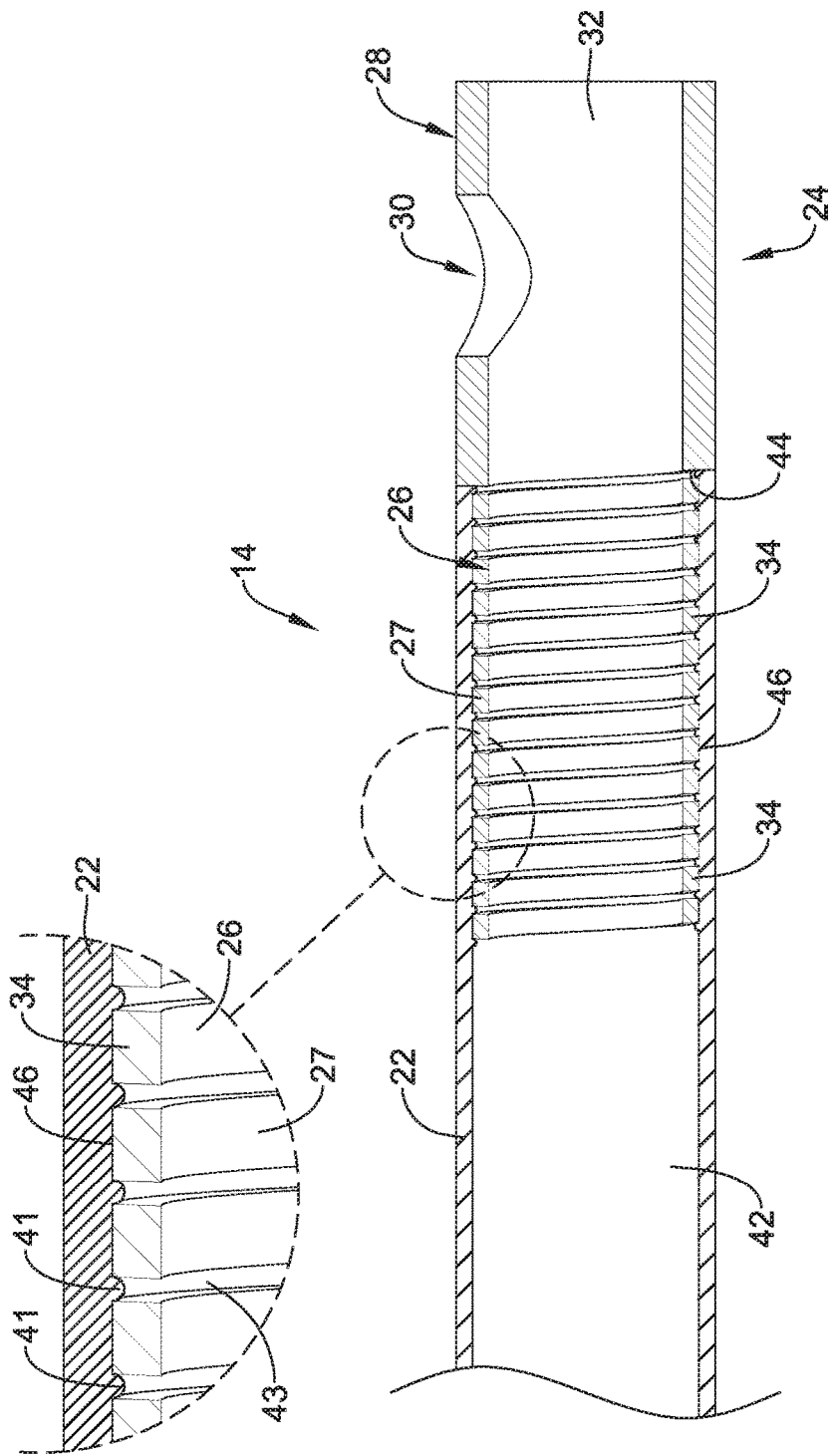
FIG. 5 is a cross-sectional view of an example tip member coupled to a tubular member.

FIG. 5 shows tubular member 22 coupled to distal tip 24 along interface region 46. While the examples disclosed herein may contemplate that tubular member 22 may be coupled to distal tip 24 via several methodologies, FIG. 5 shows tubular member 22 coupled to distal tip 24 via a melting/reflow process.

Coupling tubular member 22 to distal tip 24 via a melting/reflow process may include applying energy to tubular member 22 along the portion of tubular member 22 that extends over bonding portion 26 (as described above) such that tubular member 22 melts/reflows along bonding portion 26. Further, melting and/or reflowing tubular member 22 may cause the inner surface of tubular member 22 to extend radially inward toward the outer surface of bonding portion 26.

Additionally, in some instances the outer surface of bonding portion 26 may include one or more openings and/or apertures extending along the length of bonding portion 26. For example, the outer surface (e.g., the openings and/or apertures) of bonding portion 26 may include one or more slits, teeth, grooves, lattice, slots, texture and/or dimples. These are just examples. Other surface texture features are contemplated. As stated above, in some examples the inner surface of tubular member 22 may extend into the openings and/or apertures along the surface of bonding portion 26. For example, a region of the inner surface of tubular member 22 may extend radially inward into openings between filaments (e.g., windings) 34 of coil 27.

Further, after the period of time, the portion of tubular member 22 extending into the openings and/or apertures along bonding portion 26 may harden, thereby creating a mechanical interlock between tubular member 22 and bonding portion 26. In some instances, the mechanical interlock may be defined as the friction and/or interface fit between the inner surface of tubular member 22 and the outer surface of bonding portion 26. In some examples, the interference and/or or interlocking fit between the inner surface of tubular member 22 and bonding portion 26 may occur in the absence of adhesive.

For example, the detailed view of FIG. 5 shows tubular member 22 extending into bonding portion 26 after having been melted/reflowed and subsequently hardened. As shown in FIG. 5 (and discussed above), inwardly extending portions/regions 41 of tubular member 22 extend radially inward into openings/apertures 43 between windings 34 of coil 27. As shown, tubular member 22 may include one or more inwardly extending portions 41 that, upon hardening, may provide a mechanical interlock between tubular member 22 and bonding portion 26.

Figure 6A:
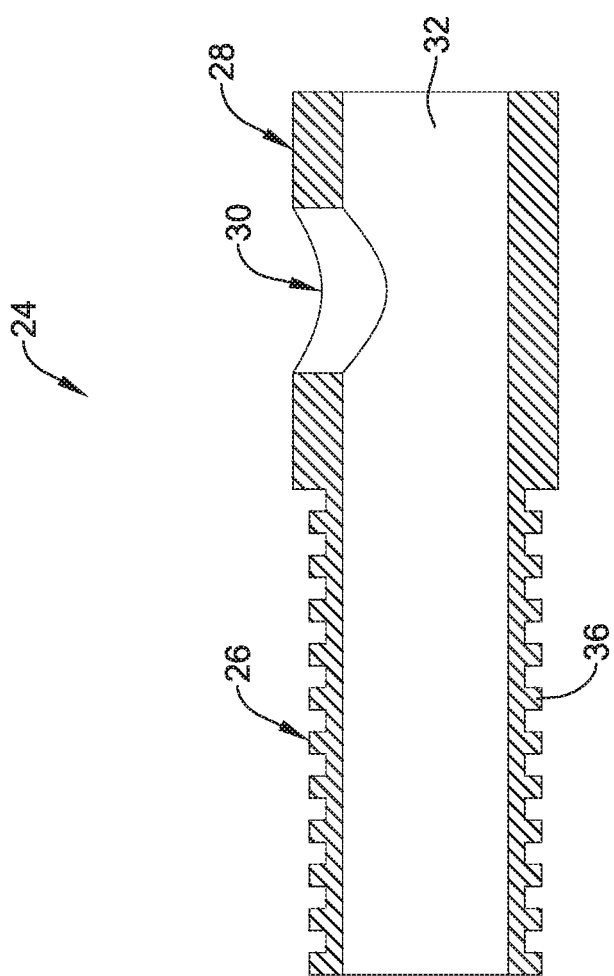
FIG. 6A is a cross-sectional view of an example tip member.
Figure 6B:
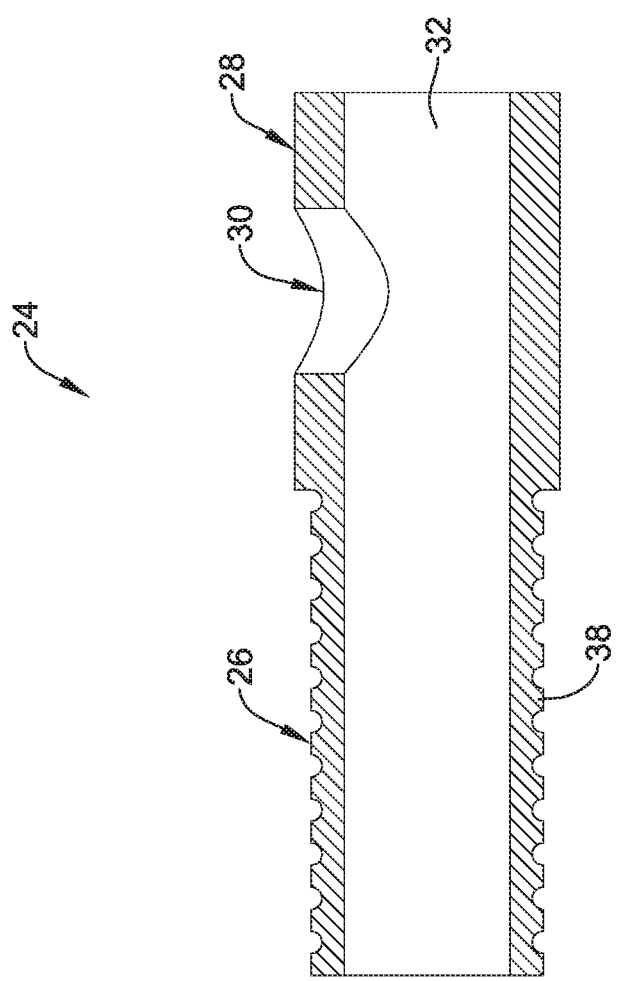
FIG. 6B is a cross-sectional view of an example tip member.
Figure 6C:
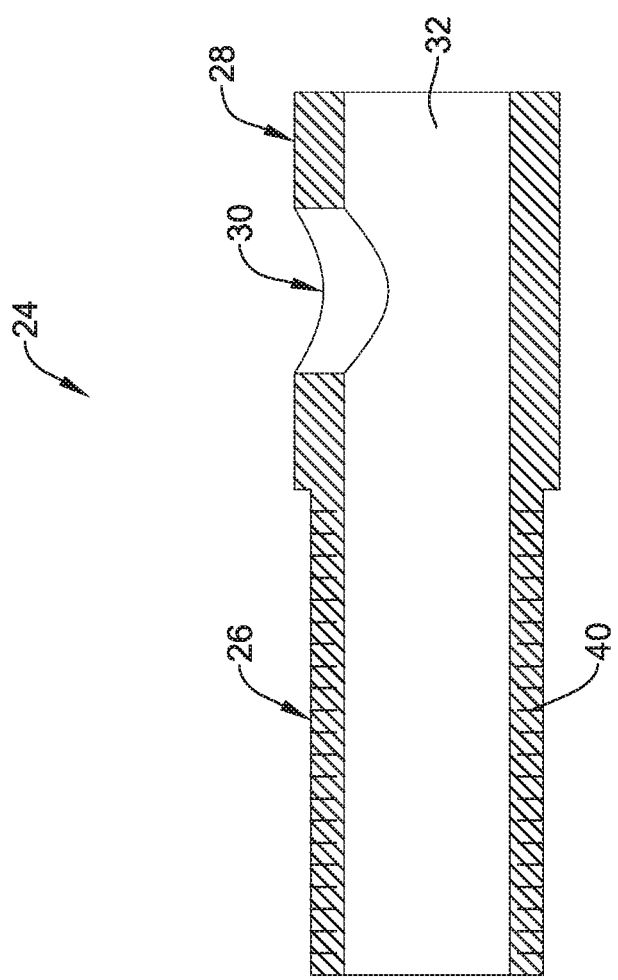
FIG. 6C is a cross-sectional view of an example tip member.
Figure 6D:
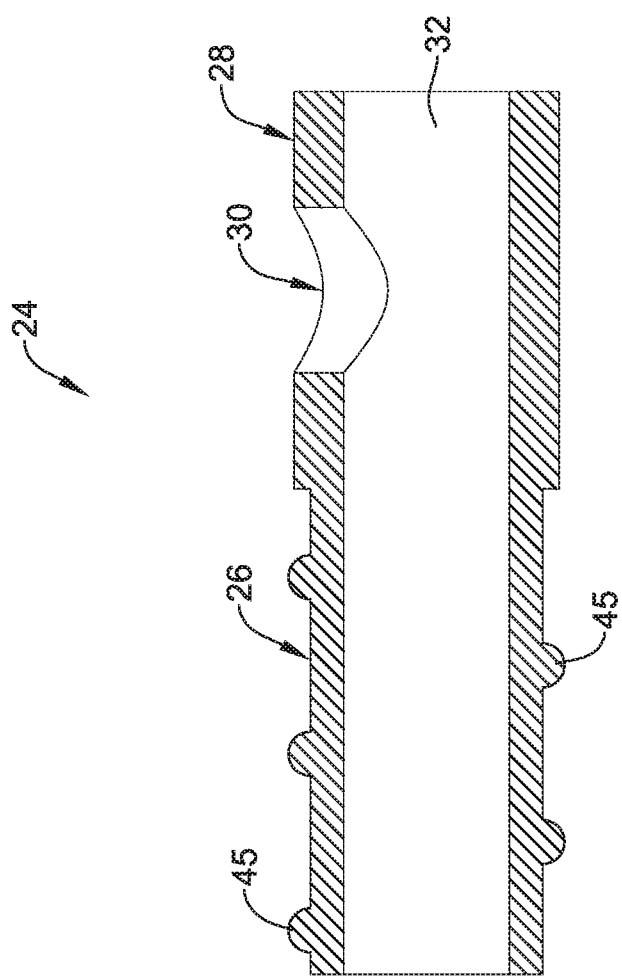
FIG. 6D is a cross-sectional view of an example tip member.

FIGS. 6A-6E illustrate additional examples of alternative openings, apertures, and/or surface textures that may be utilized on bonding portion 26. It is contemplated that while the specific design of the example bonding portions shown in FIGS. 6A-6E may differ from the coil design described above, the mechanical interlock between the tubular member 22 and bonding portion 26 may operate similarly to that described above with respect to coil member 27. For example, FIG. 6A shows a plurality of teeth 36 extending outwardly from bonding portion 26. Tubular member 22 may extend into the openings/apertures 43 between teeth 36. FIG. 6B shows another example bonding portion 26 including half-moon shaped openings/apertures 43 between teeth 38. Further, FIG. 6C shows a plurality of axial slits and/or slots 40 extending along the surface of bonding portion 26. Slits/slots 40 may extend partially or entirely through the tubular wall of the bonding portion 26. FIG. 6D shows a threaded member 45 extending radially outward from the surface of bonding portion 26. These examples are illustrative. It is contemplated that bonding portion may include many different configurations designed to mechanically interlock with tubular member 22.

Figure 6E:
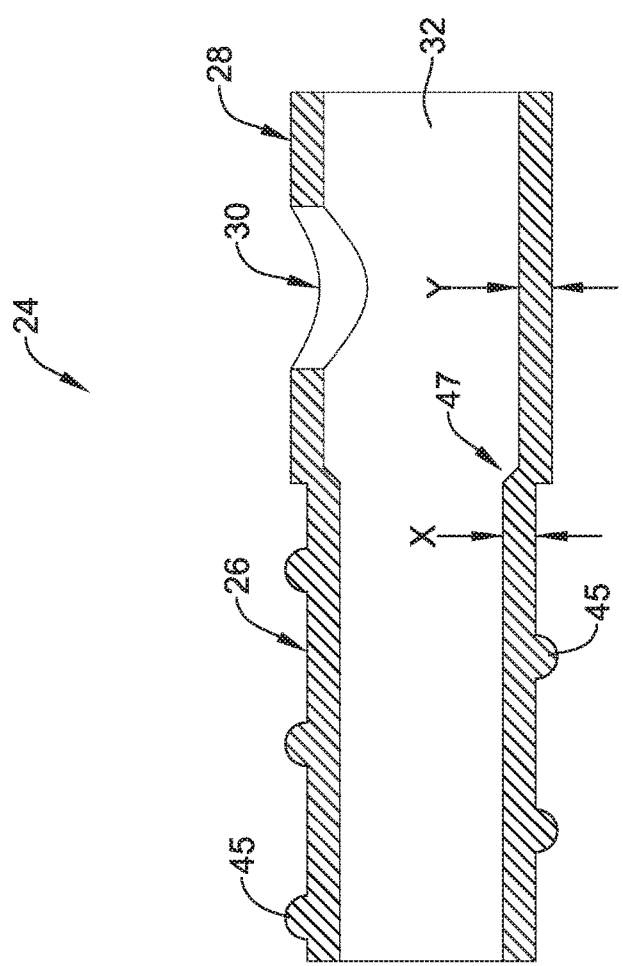
FIG. 6E is a cross-sectional view of an example tip member.

In some examples, the wall thickness of the distal tip 24 may remain substantially consistent throughout the length of the distal tip 24. For example, FIG. 6E shows distal tip 24 having bonding portion 26 and distal portion 28. Further, as shown in FIG. 6E, the wall thickness "X" of the bonding portion 26 is substantially equivalent to the wall thickness "Y" of distal portion 26. In some instances, distal tip 24 may include a distal transition section 47. The distal transition section may further include a tapered portion. It is contemplated that the examples described herein may include design features that incorporate a uniform wall thickness described with respect to FIG. 6E. However, the particular design depicted in FIG. 6E is not intended to be limiting. Rather, a uniform wall thickness may be achieved through a variety of distal tip designs (e.g., tapered, stepped, linear transition, etc.). The materials that can be used for the various components of assembly 10 (and/or other assemblies or components thereof) and the delivery devices disclosed herein may include those commonly associated with medical devices. For simplicity purposes, the following discussion makes reference to delivery system 10. However, this is not intended to limit the disclosure as the discussion may be applied to other structures or components of system 10 and/or any other suitable devices disclosed herein.

Catheters 12/14 and distal tip 24 may be made from a metal, metal alloy, polymer (some examples of which are disclosed below), a metal-polymer composite, ceramics, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties and has essentially no yield point.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, catheters 12/14 and distal tip 24 and other components of system 10 may also be doped with, made of, or otherwise include a radiopaque material. Radiopaque materials are understood to be materials capable of producing a relatively bright image (e.g., and/or otherwise a contrasted image) on a fluoroscopy screen or another imaging technique during a medical procedure. This relatively bright image aids the user of system 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of system 10 to achieve the same result.

In some embodiments, a degree of MRI compatibility is imparted into system 10. For example, to enhance compatibility with Magnetic Resonance Imaging (MM) machines, it may be desirable to make system 10 in a manner that would impart a degree of MM compatibility. For example, system 10 may be made of a material that does not substantially distort the image and create substantial artifacts (artifacts are gaps in the image). Certain ferromagnetic materials, for example, may not be suitable because they may create artifacts in an MM image. System 10 may also be made from a material that the MM machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers that may be utilized for system 10 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the polymer can contain up to about 6% LCP.

Catheters 12/14, distal tip 24 or other components of system 10 may also include a coating or covering (not shown). The covering or coating may be disposed along the interior of catheters 12/14 and distal tip 24, along the exterior of catheters 12/14 and distal tip 24, or both. The covering may be made from a polymer (including any of those listed above) or any other suitable material. In some embodiments, the covering may comprise a lubricious, hydrophilic, protective, or other type of coating. Hydrophobic coatings such as fluoropolymers provide a dry lubricity which improves device handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or covering may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present disclosure.

It should be understood that this disclosure is, in many respects, only illustrative. Changes may be made in details, particularly in matters of shape, size, and arrangement of steps without exceeding the scope of the disclosure. The disclosure's scope is, of course, defined in the language in which the appended claims are expressed.

What is claimed is:

1. An embolic coil delivery assembly, comprising:
   a tubular member having a distal portion, a proximal portion and a lumen extending therein;
   a tip member secured to the tubular member, the tip member including a distal portion and a bonding portion, the bonding portion including an outer bonding surface and an inner surface, wherein the bonding portion includes a coil, wherein the coil includes a plurality of windings; and
   an embolic coil releasably disposed within the distal portion of the tip member; wherein the distal portion of the tubular member extends over the outer bonding surface of the tip member;
   wherein the tubular member further comprises an inner surface, wherein the inner surface includes an inwardly extending member, wherein the inwardly extending member extends into a slot between two of the plurality of windings to mechanically interlock with the two of the plurality of windings, and wherein the slot extends through the outer bonding surface and the inner surface of the ponding portion;
   wherein the distal portion of the tip member further includes an aperture directed radially away from a longitudinal axis of the tip member.

2. The assembly of claim 1, wherein the distal portion of the tip member includes a first flexibility and the bonding portion includes a second flexibility different from the first flexibility.

3. The assembly of the claim 1, wherein the distal portion of the tip member includes a first wall thickness and the bonding portion of the tip member includes a second wall thickness different from the first wall thickness, wherein the second wall thickness is configured to provide a flexibility that is greater than the first wall thickness.

4. The assembly of claim 1, wherein the distal portion of the tip member includes an outer surface, and inner surface and a tubular wall extending therebetween, and wherein the aperture extends through at least a portion of the tubular wall.

5. The assembly of claim 1, wherein the tip member includes a lumen extending therein, and wherein the lumen of the tip member is substantially aligned with the lumen of the tubular member.

6. The assembly of claim 1, wherein the tubular member includes an outer diameter and wherein the distal portion of the tip member includes an outer diameter substantially equal to the outer diameter of the tubular member.

7. The assembly of claim 1, further comprising a pull wire disposed within at least a portion of the lumen of the tubular member.

8. The assembly of claim 7, wherein proximal retraction of the pull wire releases the embolic coil.

* * * * *